United States Patent
Zvietcovich Zegarra et al.

(10) Patent No.: US 11,678,801 B2
(45) Date of Patent: Jun. 20, 2023

(54) GABOR DOMAIN OPTICAL COHERENCE ELASTOGRAPHY

(71) Applicant: University of Rochester, Rochester, NY (US)

(72) Inventors: Jose Fernando Zvietcovich Zegarra, Houston, TX (US); Jannick P. Rolland, Rochester, NY (US); Cristina Canavesi, West Henrietta, NY (US); Kevin J Parker, Rochester, NY (US)

(73) Assignee: University of Rochester, Rochester, NY (US)

( * ) Notice: Subject to any disclaimer, the term of this patent is extended or adjusted under 35 U.S.C. 154(b) by 562 days.

(21) Appl. No.: 16/838,875

(22) Filed: Apr. 2, 2020

(65) Prior Publication Data

US 2021/0307611 A1     Oct. 7, 2021

(51) Int. Cl.
    *G06K 9/00*            (2022.01)
    *A61B 5/00*            (2006.01)
    (Continued)

(52) U.S. Cl.
    CPC .......... *A61B 5/0066* (2013.01); *A61B 5/0042* (2013.01); *A61B 5/0051* (2013.01);
    (Continued)

(58) Field of Classification Search
    CPC .......... A61B 2562/0242; A61B 5/0042; A61B 5/0051; A61B 5/0055; A61B 5/0068; A61B 5/441; A61B 5/7257; A61B 5/4064; A61B 5/442; A61B 5/6821; G02B 21/0028; G02B 21/0036; G02B 21/006; G02B 21/0076; G02B 21/365; G02B 6/4215; G02B 21/0056; G06T 2207/30016;
    (Continued)

(56) References Cited

U.S. PATENT DOCUMENTS

| | | | |
|---|---|---|---|
| 8,340,455 | B2 | 12/2012 | Rolland et al. |
| 11,413,007 | B2 * | 8/2022 | Ambrozinski ....... A61B 8/0858 |

(Continued)

OTHER PUBLICATIONS

Schmitt, J. M., "OCT elastography: imaging microscopic deformation and strain of tissue," Opt. Express 3(6), 199-211 (1998).

(Continued)

*Primary Examiner* — Tom Y Lu
(74) *Attorney, Agent, or Firm* — Wissing Miller LLP (57) ABSTRACT a) A Gabor domain optical coherence microscopy (GD-OCM) system providing high resolution of structural and motion imaging of objects such as tissues is combined with the use of reverberant shear wave fields (RevSW) or longitudinal shear waves (LSW) and two novel mechanical excitation sources: a coaxial coverslip excitation (CCE) and a multiple pronged excitation (MPE) sources providing structured and controlled mechanical excitation in tissues and leading to accurate derivation of elastographic properties. Alternatively, general optical computed tomography (OCT) is combined with RevSW or LWC in the object to derive elastographic properties. The embodiments include (a) GD-OCM with RevSW; (b) GD-OCM with LSW; (c) General OCT with RevSW; and General OCT with LSW.

5 Claims, 10 Drawing Sheets

(51) Int. Cl.
G02B 21/00 (2006.01)
G02B 6/42 (2006.01)
G02B 21/36 (2006.01)
G06T 7/00 (2017.01)

(52) U.S. Cl.
CPC .......... *A61B 5/0055* (2013.01); *A61B 5/0068* (2013.01); *A61B 5/441* (2013.01); *G02B 6/4215* (2013.01); *G02B 21/006* (2013.01); *G02B 21/0028* (2013.01); *G02B 21/0036* (2013.01); *G02B 21/0076* (2013.01); *G02B 21/365* (2013.01); *G06T 7/0012* (2013.01); *A61B 5/7257* (2013.01); *A61B 2562/0242* (2013.01); *G06T 2207/30016* (2013.01); *G06T 2207/30041* (2013.01); *G06T 2207/30088* (2013.01)

(58) Field of Classification Search
CPC . G06T 2207/30041; G06T 2207/30088; G06T 7/0012; G06T 2207/10016; G06T 2207/10028; G06T 2207/10056; G06T 2207/10101; G06T 2207/20056; G06T 5/10
See application file for complete search history.

(56) References Cited

U.S. PATENT DOCUMENTS

| | | | |
|---|---|---|---|
| 2018/0008236 A1* | 1/2018 | Venkataraman | A61B 8/5246 |
| 2018/0260952 A1* | 9/2018 | Bagherinia | A61B 3/102 |
| 2020/0352437 A1* | 11/2020 | Yang | A61B 3/0025 |
| 2021/0018606 A1* | 1/2021 | McCaw | G01S 7/52042 |
| 2021/0178194 A1* | 6/2021 | Sverdlik | A61N 7/00 |

OTHER PUBLICATIONS

Wang, S., and Larin, K. V., "Optical coherence elastography for tissue characterization: a review," Journal of biophotonics 8(4), 279-302 (2015).

Mulligan, J. A., Untracht, G. R., Chandrasekaran, S. N., Brown, C. N., and Adie, S. G., "Emerging Approaches for High-Resolution Imaging of Tissue Biomechanics With Optical Coherence Elastography," IEEE Journal of Selected Topics in Quantum Electronics 22(3), 246-265 (2016).

Larin, K. V., and Sampson, D. D., "Optical coherence elastography—OCT at work in tissue biomechanics [Invited]," Biomed. Opt. Express 8(2), 1172-1202 (2017).

Kirby, M. A., Pelivanov, I., Song, S., Ambrozinski, L., Yoon, S. J., Gao, L., Li, D., Shen, T. T., Wang, R. K., and O'Donnell, M., "Optical coherence elastography in ophthalmology," J Biomed Opt 22(12), 1-28 (2017).

Parker, K. J., Doyley, M. M., and Rubens, D. J., "Imaging the elastic properties of tissue: the 20 year perspective," Physics in Medicine & Biology 56(1), R1.

Streitberger, K.-J., Reiss-Zimmermann, M., Freimann, F. B., Bayerl, S., Guo, J., Arlt, F., Wuerfel, J., Braun, J., Hoffmann, K.-T., and Sack, I., "High-Resolution Mechanical Imaging of Glioblastoma by Multifrequency Magnetic Resonance Elastography," PLOS One 9(10), e110588 (2014).

Egle, D. M., "Diffuse wave fields in solid media," The Journal of the Acoustical Society of America 70(2), 476-480 (1981).

Rolland, J. P., Meemon, P., Murali, S., Thompson, K. P., and Lee, K.-s., "Gabor-based fusion technique for Optical Coherence Microscopy," Opt. Express 18(4), 3632-3642 (2010).

Zvietcovich, F., Rolland, J. P., and Parker, K. J., "An approach to viscoelastic characterization of dispersive media by inversion of a general wave propagation model," Journal of Innovative Optical Health Sciences 10(06), 1742008.

Song, S., Huang, Z., and Wang, R. K., "Tracking mechanical wave propagation within tissue using phasesensitive optical coherence tomography: motion artifact and its compensation;" BIOMEDO 18(12), 121505 (2013).

Parker, K. J., Ormachea, J., Zvietcovich, F., and Castaneda, B., "Reverberant shear wave fields and estimation of tissue properties," Phys Med Biol 62(3), 1046-1061 (2017).

Zvietcovich, F., Rolland, J. P., Yao, J., Meemon, P., and Parker, K. J., "Comparative study of shear wave-based elastography techniques in optical coherence tomography," BIOMEDO 22(3), 035010-035010 (2017).

Hoyt, K., Castaneda, B., and Parker, K. J., "Two-Dimensional Sonoelastographic Shear Velocity Imaging," Ultrasound in Medicine & Biology 34(2), 276-288 (2008).

Wang, S., and Larin, K. V., "Noncontact depth-resolved micro-scale optical coherence elastography of the cornea," Biomed. Opt. Express 5(11), 3807-3821 (2014).

Singh, M., Li, J., Han, Z., Vantipalli, S., Liu, C. H., Wu, C., Raghunathan, R., Aglyamov, S. R., Twa, M. D., and Larin, K. V., "Evaluating the Effects of Riboflavin/UV-A and Rose-Bengal/Green Light Cross-Linking of the Rabbit Cornea by Noncontact Optical Coherence Elastography," Invest Ophthalmol Vis Sci 57(9), OCT112-120 (2016).

Scarcelli, G., Pineda, R., and Yun, S. H., "Brillouin Optical Microscopy for Corneal Biomechanics," Investigative Ophthalmology & Visual Science 53(1), 185-190 (2012).

Nahas, A., Bauer, M., Roux, S., and Boccara, A. C., "3D static elastography at the micrometer scale using Full Field OCT," Biomed Opt Express 4(10), 2138-2149 (2013).

Hollman, K. W., Emelianov, S. Y., Neiss, J. H., Jotyan, G., Spooner, G. J. R., Juhasz, T., Kurtz, R. M., and O'Donnell, M., "Strain Imaging of Corneal Tissue With an Ultrasound Elasticity Microscope," Cornea 21(1), 68-73.

Shih, C.-C., Huang, C.-C., Zhou, Q., and Shung, K. K., "High-Resolution Acoustic-Radiation-Force-Impulse Imaging for Assessing Corneal Sclerosis," IEEE transactions on medical imaging 32(7), 1316-1324 (2013).

Canavesi, C, and Rolland, J.P., "Ten Years of Gabor Domain Coherence Micrography," Appl. Sci. 2019, 9, 2565.

* cited by examiner

Fig. 5a  Rev-3D OCE Method

Fig. 5b  Lamb Wave Method

GABOR DOMAIN OPTICAL COHERENCE ELASTOGRAPHY

GOVERNMENT RIGHTS

This invention was made with the government support under Grant number IIP-1534701 awarded by the National Science Foundation. The government has certain rights in the invention.

FIELD

This patent specification relates to characterizing properties of material using elastography, more specifically optical coherence elastography such as Gabor domain optical coherence elastography.

BACKGROUND

Several references are cited at the end of this patent specification and are identified by a number in parenthesis in the body of this patent specification. They are hereby incorporated by reference.

Elastography typically involves creating a mechanical perturbation in a material such as tissue, observing the tissue response to infer its properties, and displaying results, usually as an image. There are many applications of this basic techniques, for example to differentiate between normal breast tissue and certain lesions that typically are stiffer and respond differently to mechanical perturbation induced for example by low frequency vibration. Elastography using optical coherence tomography (OCT), also known as optical coherence elastography (OCE), as discussed by Schmitt in 1998 (1), is a technique that uses low coherence interferometry to measure mechanical perturbations. Together, with the evolution of OCT systems from time-domain to frequency-domain, many OCE techniques have been proposed for characterizing tissue mechanics (Young's modulus) and their implications in pathophysiology, diagnostics, surveillance, and therapeutics of disease. Examples of development include improvements on loading methods, OCT acquisition protocols, physical models and approaches to measuring viscoelastic properties of tissue, post-processing pipelines, and estimation methods.

Much of OCE work has been studied and categorized in review papers in the years 2015 (2), 2016 (3), and 2017 (4, 5). Here, taxonomical classification of OCE methods are conducted according to various categories: spatial and temporal extent of loading, excitation approaches, and applications in biological tissues. Among various types of OCE methods, dynamic OCE leverages the propagation of mechanical waves measured using an OCT system for the elastography of tissues. Using the typical mechanical excitation methods, perturbation wavelengths, and OCT systems reported in the literature review, surface acoustic waves (SAW) are the predominant perturbation, diminishing the capabilities of OCE in (1) detecting elasticity gradients along the axial direction (composite materials), and (2) providing accurate qualitative elasticity information of tissues independently of their boundary conditions.

Pure shear waves can propagate in infinite media (when no boundaries with other media are present such as air). Typically, ultrasound (US) or magnetic resonance (MRI) imaging systems can obtain images deeper in the tissue where the infinite media assumption is satisfied. (6, 7) However, optical imaging systems (e.g. OCT and optical microscopy) are constrained to few millimeters of depth of field and the field of view (FOV) usually includes the tissue, its boundary and the coupling media (i.e. air, gel, or fluid). This type of boundary condition is known as semi-infinite media, which mostly generates SAW. In the majority of dynamic OCE methods, shear wave propagation is desired since its speed ($c_s$) is related to the shear modulus (G) of the media (neglecting viscosity) by $$c_s = \sqrt{G/\rho}, \qquad \text{eq. 1}$$

where $\rho$ is the density of the medium. Then, G can be related to Young's modulus (E) by using $$G = E/2(1+\nu), \qquad \text{eq. 2}$$

for linear, homogeneous and isotropic materials with a Poisson's ratio $\nu$. Typically, soft tissues are conformed mostly by water, which is uncompressible ($\nu \approx 0.5$). Then, Equation 2 can be simplified as $G = E/3$. Thus, shear waves can change their speed in material gradients of any distribution, which enables the elastic characterization of tissue by estimating the local $c_s$.

SUMMARY OF DISCLOSURE

In dynamic OCE, shear wave propagation has been complicated to achieve due to difficulties in ensuring infinite-media boundary conditions for the given excitation wavelength. To overcome these problems, dynamics approaches can be used such as: reverberant shear wave (RevSW) fields created by a multiple pronged excitation (MPE) source; and longitudinal shear waves (LSW) created by a coaxial coverslip excitation (CCE) source. In both cases, mechanical excitations can be generated at elevated frequencies (~2 to 10 kHz). LSW can be generated at the surface of the tissue and propagate through depth with desirable properties for OCE: (a) LSW travel at the shear wave speed (and it can be converted into shear or Young's modulus using Eq. 1 and Eq. 2) and can discriminate elasticity gradients along depth, and (b) displacement of LSW is longitudinally polarized along the direction of propagation; therefore, it can be measured by any phase-sensitive OCT system. RevSW fields are produced by the harmonic (continuous) interaction of multiple shear waves travelling across all possible directions. (8) These fields promote the propagation of a higher ratio of shear waves in semi-infinite tissue type compared to transient excitation in which SAWs are mostly dominant. Their existence can bring two important advantages in tissue characterization: shear speed can be easily converted into shear or Young's moduli using Eq. 1 and Eq. 2, and elasticity gradients along the depth axis (perpendicular to the propagation direction of SAW) can be detected with much better contrast. Both wave approaches can enable layer characterization of tissues such as the skin and the cornea with important applications in the diagnosis and monitoring of diseases and treatments.

The implementation of LSW and RevSW frameworks into OCE gives birth to a novel approach based on the integration of three innovative components carefully tailored for the accurate elastography of tissues: (a) A Gabor domain optical coherence microscopy (GD-OCM) system accounting for a high resolution of structural and motion imaging of tissues; (b) a mathematical framework accounting for the physics of mechanical wave propagation in LSW and RevSW, and the development of image processing based estimators; and (c) two novel mechanical excitation sources: CCE, and MPE, for structured and controlled mechanical excitation in tissues. Finally, experimental results support benefits of the new approach compared to other state of the art OCE methods, highlighting the contribution and innovation level of the Gabor domain optical coherence elastography (GD-OCE) described in this patent specification.

According to some embodiments, a Gabor domain optical coherence elastography system comprises: a source configured to induce reverberant shear waves (RevSW) in a field of view (FOV) of an object; a Gabor domain optical coherence microscope configured to observing the object and to detect displacement of locations in said FOV in the object over a selected time interval in the presence of said RevSW in the FOV of the object; and a processor system configured to computer-process said displacements to derive and display elastographic properties of said FOV in the object. The source of said RevSW field can comprise a multi-pronged device contacting two or more different sites on or coupled with the object and the object can be the cornea of an eye or a patient or animal's skin or brain tissue In some embodiments, a Gabor domain optical coherence elastography system is otherwise similar but the source is configured to induce longitudinal shear waves (LSW) in a three-dimensional (3D) field of view (FOV) in an object rather than RevSW, and a Gabor domain optical coherence microscope is configured to observe the object and to detect displacement of locations said FOV in the object over a selected time interval in the presence of said LWS in the object rather than in the presence of RevSW. The source of LWS can comprise a coverslip contacting the object over said FOV and the object can be an eye's cornea or a patient or animal's skin or brain tissue.

In some embodiments, an optical coherence elastography system comprises: a source configured to induce reverberant shear waves (RevSW) in a field of view (FOV) of an object; an optical coherence tomography instrument configured to observe the object and to detect displacement of locations in said FOV in the object over a selected time interval in the presence of said RevSW in the FOV of the object; and a processor system computer-configured to process said displacements to derive and display elastographic properties of said FOV in the object. The source of said RevSW field can comprise a multi-pronged device contacting two or more different sites on or coupled with the object and the object can be the cornea of an eye or a patient or animal's skin or brain tissue.

In some embodiments, an optical coherence elastography system is otherwise like the system in the immediately preceding paragraphs but the source is configured to induce longitudinal shear waves (LSW) in the three-dimensional (3D) field of view (FOV) in an object rather than RevSW. In this case, the source inducing LWS in the object can comprise a coverslip contacting the object over said FOV. The object and the object can be the cornea of an eye or a patient or animal's skin or brain tissue.

BRIEF DESCRIPTION OF THE DRAWINGS

FIGS. 5a and 5b show numerical simulation results of a 3D finite element model of cornea composed of four layers with differentiated linear elastic materials.

FIGS. 6a-6d show Rev3D-OCE results in ex vivo porcine cornea using a 2 kHz sinusoidal steady-state excitation and a PhS-OCT system: FIG. 6a-left shows an acquired B-mode 3D volume and FIG. 6a-right shows particle velocity reverberant volume of cornea.

FIG. 8a shows dispersion analysis of wave speed in Lamb wave method in cornea subjected to four IOP levels: 10.24, 15.80, 20.50, and 25.25 mmHg. The curves indicate that the antisymmetric zero-order Lamb wave is the most predominant given the excitation shape and boundary conditions. FIG. 8b sows a comparison of depth-dependent wave speed profiles in Rev3D-OCE and Lamb wave method in cornea subjected to four IOP levels. Lamb wave speed profiles were calculated at a frequency $f_0 = 800$ Hz to cover for all four IOP cases in FIG. 8a.

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all these details. Moreover, for the purpose of clarity, certain technical material that is known in the related art has not been described in detail in order to avoid unnecessarily obscuring the new subject matter described herein. Individual features of one or several of the specific embodiments described herein can be used in combination with features of other described embodiments or with other features. Further, like reference numbers and designations in the various drawings indicate like elements.

Gabor domain optical coherence microscopy (GD-OCM) is an imaging technology that builds on the high-speed imaging of, e.g., 80 kHz (A-line rate) provided by FD-OCT, the high axial resolution of e.g. 2.5 µm measured in air, and high lateral resolution of e.g. 2 µm throughout a FOV of 2 mm cube sample enabled by the innovative dynamic focus microscope apparatus. (9) GD-OCM has the ability of real-time (e.g., 100 ms for each focus position) refocusing of a custom-designed dynamic focusing microscope objective, and a Gabor-based fusion algorithm to produce a high lateral resolution image throughout the depth of imaging. Driven by the capability of the technique to image at high spatial and temporal resolution, the implementation of the MB-mode acquisition protocol (10) is capable of high sensitivity and resolution reconstruction of motion (displacement fields) of the full depth image based on the concept of Doppler phase shift, inverse local Fourier transform and the Gabor's signal expansion. LighTopTech, a company in Rochester, N.Y., offers a GD-OCM system.

Figure 1:
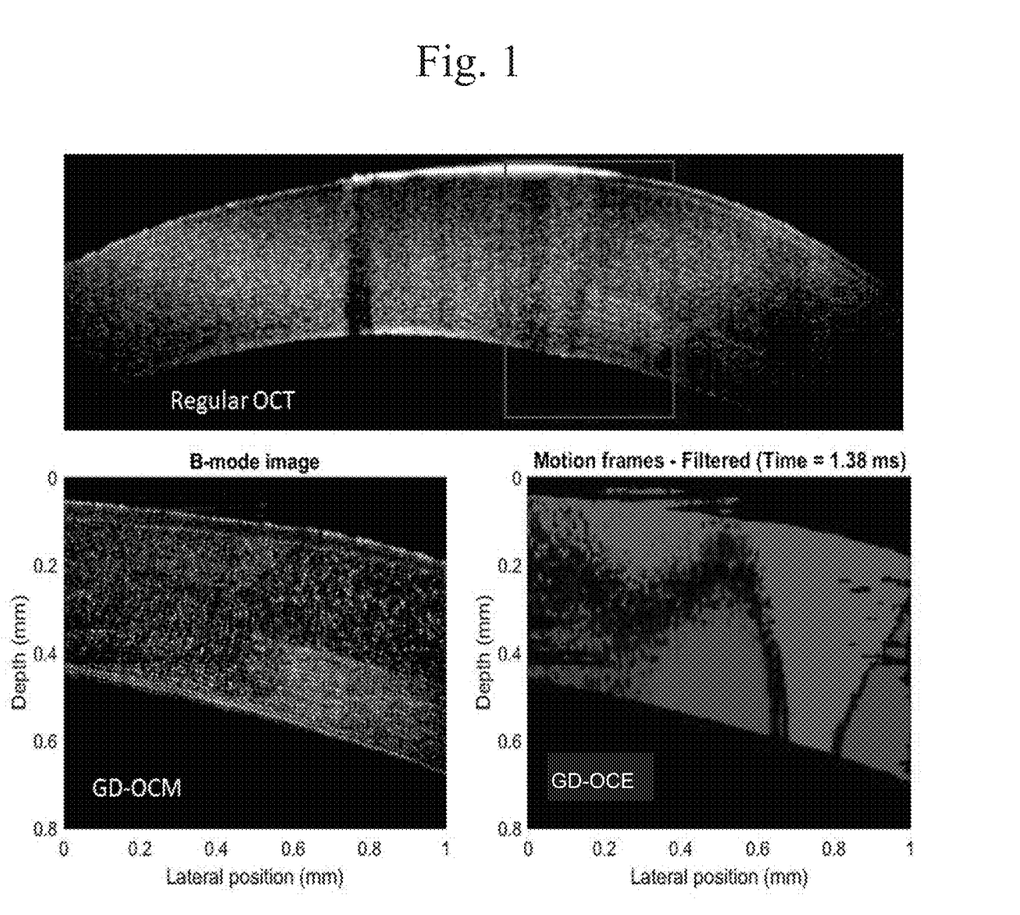
FIG. 1 shows a qualitative comparison between GD-OCM and regular OCT in terms of FOV and spatial resolution in detecting small microstructures in ex-vivo rabbit cornea. The red box indicates the FOV of GD-OCM. Color in GD-OCM motion frame corresponds to particle velocity (motion) in arbitrary units: red (axial positive), blue (axial negative) motion.

FIG. 1 shows a qualitative comparison between regular OCT and GD-OCM in terms of spatial resolution and FOV. The upper portion is labeled Regular OCT and the rectangle therein indicates the field of view, FOV, of GD-OCM. The lower left frame is labeled GD-OCM and shows a GD-OCM image of the FOV. The lower right frame shows particle velocity (motion) in arbitrary units: red (axial positive), blue (axial negative) motion, at an instant of time.

Reconstruction of displacement (or particle velocity) fields within a sample is fundamental in dynamic OCE since it enables the measurement of mechanical wave propagation. In elastography, the ability of detecting small elasticity gradients (elastography resolution) is limited by the quality of wave measurement with the imaging system (dependent on the spatial and temporal resolution of the OCT system), and how small is the wavelength of the perturbation compared to the target elasticity gradient in the sample (inversely dependent on the frequency of excitation used to produce waves). Therefore, in order to achieve higher elastography resolution, the excitation frequency can be increased to thereby produce smaller size wavelength patterns within the same FOV, compromising accurate spatial measurement of waves when a conventional OCT system is used (lateral resolution ~20 µm). Moreover, if we consider that mechanical wave attenuation strongly increases when the excitation frequency is elevated, the motion measurement is strongly compromised when using a conventional OCT system. GD-OCM has unique capabilities in resolution and sensitivity that allows the elastography of tissues at higher excitation frequency by compensating with a higher spatial resolution and sensitivity to motion; therefore, increasing the elastography resolution.

Tissue or material excitation. Most of the excitation techniques used in dynamic OCE as reported in the known literature produce a transient (along the temporal extent) and single localized (along the spatial extent) mechanical excitation which produces waves propagating planarly, cylindrically or spherically within the tissue. (4) However, due to the boundary conditions of tissues, and the spatio-temporal nature of wave propagation, SAW (and not shear waves) are the dominant perturbation. This patent specification makes use of two novel excitation devices: MPE and CCE sources.

Multiple pronged excitation source. An example of a multiple pronged excitation, MPE, source is a device able to produce RevSW fields. This device contains N>2 (e.g., 8) equidistant and circular distributed rods around a ring border. Each rod is attached to a single piezo electric actuator capable of producing vibrations with different excitation frequencies and temporal phases.

Figure 2:
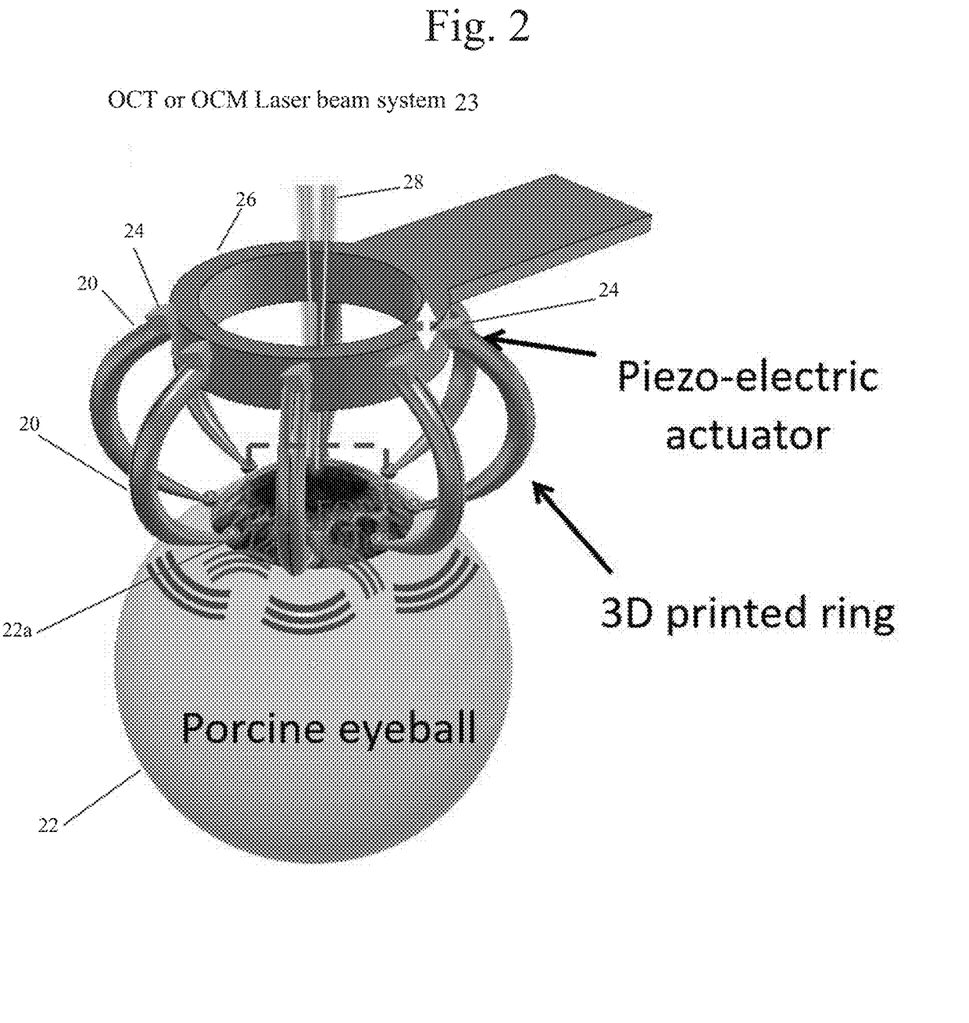
FIG. 2 is a perspective view of an example of MPE source with N=8 independent rods for the creation of RevSW fields in a cornea according to some embodiments, using an OCT or GD-OCM laser beam system.

FIG. 2 shows an example where N=8 rods 20 are slightly touching the corneal epithelium 22a of an eye 22 (as an example of tissue) in a concentric configuration and produce reverberant fields when the piezo electric actuators 24 are excited. The ring shape 26 allows the imaging of the cornea using the GD-OCM system using OCT laser beam 28, while the rods 20 introduce mechanical excitation. The rod tips can be polished to avoid damaging the cornea. Another embodiment places the rods on external tissue surrounding the eye, thus avoiding any physical contact between the rods 20 and the eye 22. An OCT or GD-OCM laser beam system 23 includes a laser beam source and detector and a computer system to control the beam and to process the information in the return laser beam and display results The MPE device can produce RevSW fields in tissue by exciting each independent piezo electric actuator 24 with the same excitation frequency at random temporal phases. It also allows the structured excitation of tissues with any given frequency and phase distribution for other elastography applications. For instance, each actuator 24 can be independently excited while the other, remaining actuators 24 rest in order to measure SAW propagation at a certain direction. This protocol can be used for anisotropic studies of tissue in which each propagation direction of the SAW has a different speed.

Coaxial excitation source. A coaxial excitation source, CCE, is a device able to produce LSW propagation. Such device consists in a piezoelectric actuator fixed to the top surface of a circular glass coverslip (Thermo Fisher Scientific, Waltham, Mass., USA). The coverslip material is not restricted to glass, but any other material that allows imaging using the typical OCT light wavelengths. The bottom surface of the glass coverslip is touching the sample. An OCT or GD-OCM laser beam system 39, shown in FIG. 3b, can be used to detect and process the laser beam information and display results.

Figure 3A:
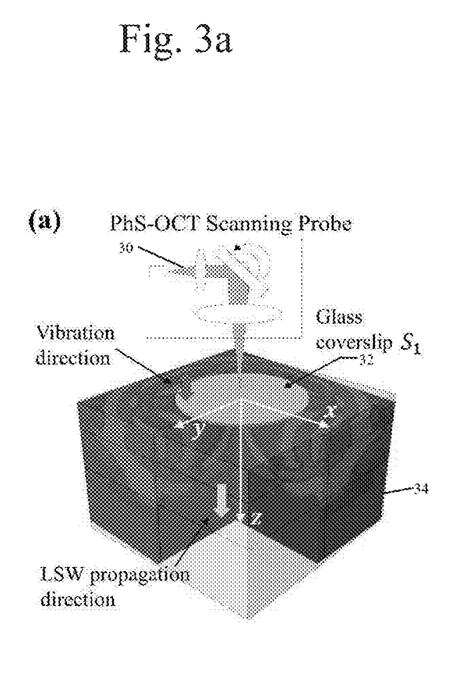
FIG. 3a is a perspective view illustrating a circular glass coverslip touching a volume sample in a 3D environment and FIG. 3b is a sectional view of scanning probe using OCT or GD-OCM for analyzing waves generated in the sample and particle velocities, according to some embodiments.
Figure 3B:
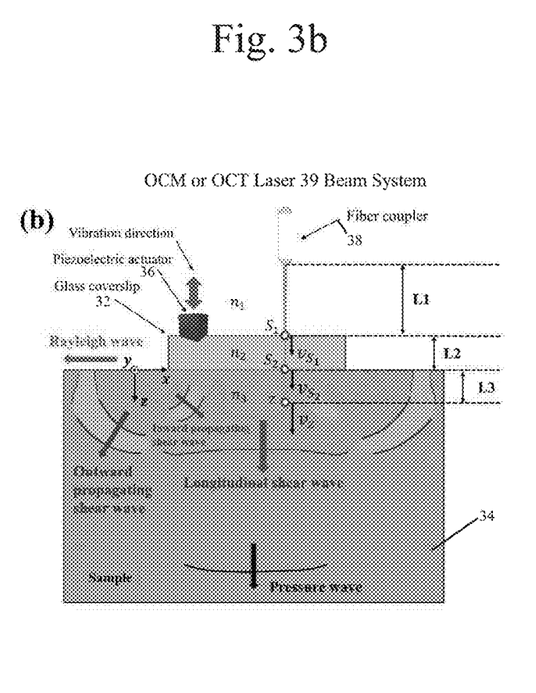

As seen in FIGS. 3a and 3b, an OCT laser beam 30 passes through a glass coverslip 32 vibrating along the axial direction z for the generation and measurement of LSW. Distortion in the phase information of OCT A-lines generated by the movement of the glass plate 32 is modeled and compensated. Methodologically, in a medium with refractive index n, the depth-dependent phase difference $\Delta\phi(z)=\phi(z,t_1)-\phi(z,t_0)$ of a given A-line at two consecutive instants $t_0$ and $t_1$ ($t_0<t_1$) for a given lateral $x_0$ position, is related to particle velocity $v_z(z)$ in the axial direction by $$v_z(z) = \Delta\phi(z)\frac{\lambda_0}{4\pi n T_s}, \qquad \text{Eq. 3}$$

where $\phi$ is the phase of the A-line signal acquired with a phase sensitive optical coherence tomography, PhS-OCT, system, n is the refractive index of the medium, $\lambda_0$ is the center wavelength of the laser, and $T_s$ is the time sampling resolution. In practice, given the experimental setup, three media with different refractive indexes are concatenated coaxially as shown in FIG. 3b: coupling air above glass coverslip 32, then glass coverslip 32, then sample 34. $\phi\phi(z)$ measurements (and, therefore, $v_z(z)$) can be affected by the motion of surfaces within transition of materials. An appropriate model to compensate for those effects and estimate the true phase difference $\Delta\phi_T(z)$ produced by any scattered within the sample is presented as $$\Delta\phi_T(z) = \Delta\phi(z) + \left(\frac{n_3}{n_2} - 1\right)\Delta\phi(s_2) + \left(\frac{n_3}{n_1} - \frac{n_3}{n_2}\right)\Delta\phi(s_1), \quad \text{Eq. 4}$$

where $\Delta\phi(z)$, $\Delta\phi(s_1)$, and $\Delta\phi(s_2)$ are phase differences measured at the sample, the boundary between the sample 34 and the bottom surface of the glass coverslip 32, and the boundary between the top surface of glass coverslip 32 and air, respectively. Also, $n_1$, $n_2$, and $n_3$, are the refractive indexes of air, the glass coverslip, and the sample, respectively. Assuming the glass coverslip is rigid, then $\Delta\phi(s_2)=\Delta\phi(s_1)$, and Equation 4 reduces to $$\Delta\phi_T(z) = \Delta\phi(z) + \left(\frac{n_3}{n_1} - 1\right)\Delta\phi(s_1), \quad \text{Eq. 5}$$

which is the same correction factor as found in (11) for a two-media configuration (air and sample). The coverslip material is not restricted to glass but can be another material that allows imaging using the OCT typical wavelengths of light. The coverslip can be integrated with the GD-OCM microscope. In the case of using a common-path interferometric scheme, surface $S_1$ or $S_2$ in FIG. 3b can be used as the reference signal; in this case Equation 5 is not needed anymore since the compensation has been conducted in hardware.

In FIG. 3a, the irregularly shaped regions red in sample 34 illustrate particle velocity (motion) in axial positive direction and the blue regions adjacent thereto illustrate particle velocity in axial negative direction, in each case in arbitrary units and at an instant of time. In FIG. 3b, respectively labeled arrows illustrate directions of a Raleigh wave, a longitudinal shear wave, an inward propagating shear wave, an outwardly propagating shear wave, and a pressure wave. FIG. 3b schematically shows a piezoelectric actuator acting on glass coverslip 32, and a fiberoptic coupler 38 of an OCT scanning probe analyzing waves generated in sample 34 and particle velocities measured by OCT.

Reverberant shear wave fields. A RevSW field can be understood as the superposition of planar shear waves incident from all directions that produce a particle velocity vector field $V_z(\varepsilon,t)$ at a position $\varepsilon$ and time t. (12) Typically, OCT systems measure particle velocity or displacement in one single axis, which we call the measurement axis $\hat{e}_z$. Then, the measured particle velocity is a scalar field described by $$V_z(\varepsilon,t) = V(\varepsilon,t)\cdot\hat{e}_z. \quad \text{Eq. 6}$$

Following Parker et al. (12) derivation of the spatial autocorrelation, $V_z(\varepsilon,t)$, along any direction orthogonal to the measurement axis $\hat{e}_z$ such as $\hat{e}_x$ (or $\hat{e}_y$), provides the following closed-form analytical solution:

$$B_{V_zV_z}(\Delta\varepsilon_x) = \langle V^2\rangle_{avg}\left[j_0(\beta k\Delta\varepsilon_x) - \frac{j_1(\beta k\Delta\varepsilon_x)}{\beta k\Delta\varepsilon_x}\right] \quad \text{Eq. 7}$$

where $B_{V_zV_z}$ is the spatial autocorrelation of $V_z(\varepsilon,t)$, $\langle V^2\rangle_{avg}$ is the mean squared scalar value of particle velocity, $j_0$ and $j_1$ are the spherical Bessel functions of the first kind of zero and first order, respectively; and $\Delta\varepsilon_x=\Delta\varepsilon\cdot\hat{e}_x$, with $\hat{e}_x$ being a unit vector along the x-axis. In Eq. 7, k is the local wave number that can be estimated by fitting autocorrelation profiles. The correction parameter $\beta$ compensates for the coupling media at the surface of the sample. For instance, $\beta=0.95$ when coupling media is air or vacuum, and $\beta=0.84$ for coupling media being a nearly incompressible fluid such as water. Therefore, given the excitation frequency $\omega_0$ of the reverberant field, local shear wave speed is calculated using $c_s=\omega_0/k$; and, assuming a homogeneous and isotropic material, the shear modulus can be calculated using Eq. 1 as $G=c_s^2\rho$.

Figure 4:
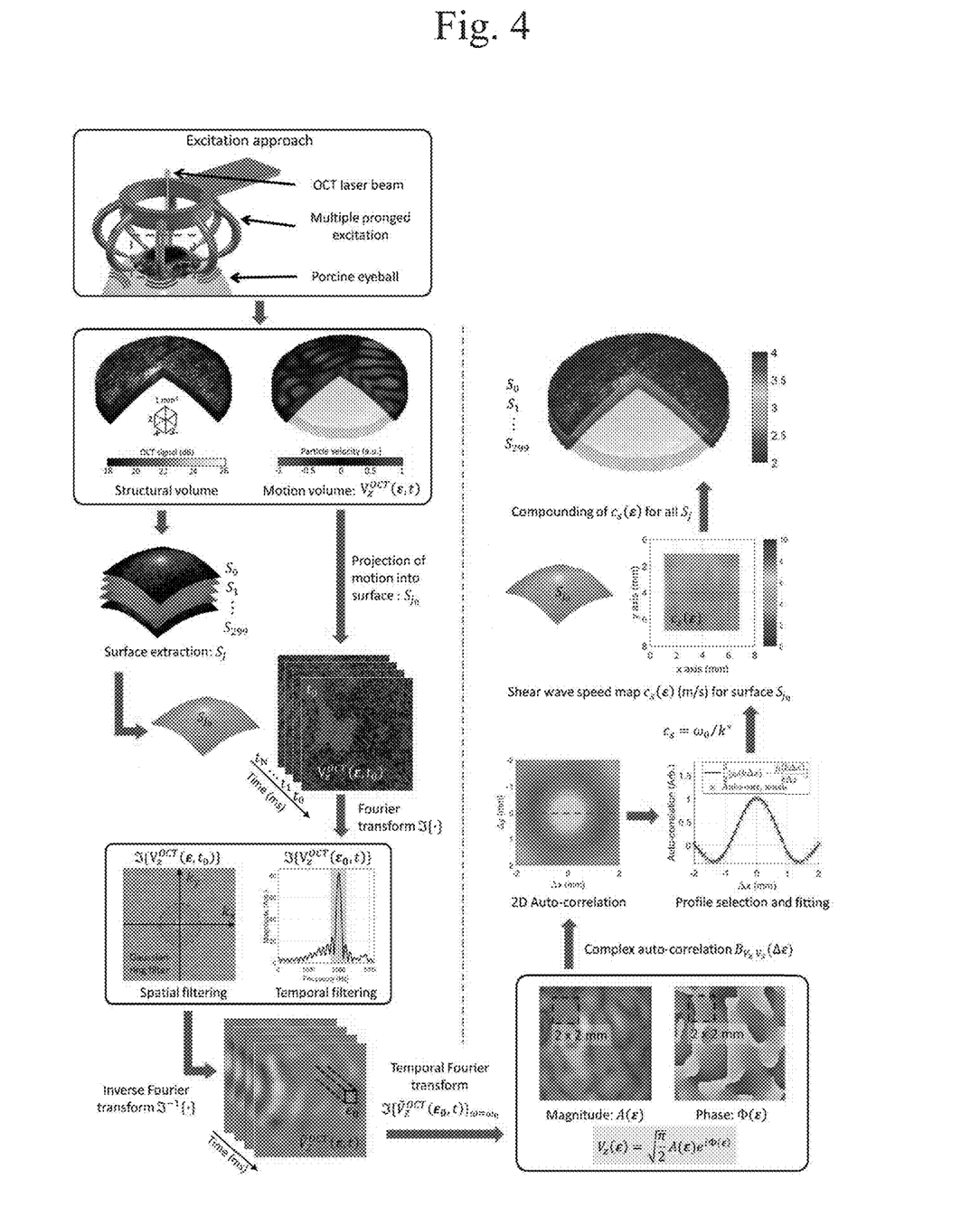
FIG. 4 illustrates a signal processing pipeline for the calculation of local shear wave speed in a volumetric sample subjected to a reverberant shear wave field excited at wo angular frequency. Eq. 2 is used for the complex auto-correlation fitting, according to some embodiments.

FIG. 4 illustrates a signal processing pipeline for the calculation of local shear wave speed in a volumetric sample subjected to a reverberant shear wave field excited at $\omega_0$ angular frequency. Equation 2 is used for the complex auto-correlation fitting. (4) Red and blue regions show, as in FIGS. 1 and 3a, particle velocity (motion) in arbitrary units: red (axial positive) and blue (axial negative) motion at an instant of time. To recover local shear wave speed within a volume subjected to a RevSW field using Equation 7, in one embodiment a full signal processing approach accounts for GD-OCM characteristics for motion calculation (motion provided just along axial direction), and motion compensations (along the boundary between the sample and the air because of the big mismatch of refractive indices). GD-OCM provides structural (a single 3D volume) and motion (a sequence of 3D volumes representing particle velocity) information of the sample subjected to a reverberant field. The top left box in FIG. 4 shows the example of FIG. 2. The next block down illustrates on left a structural volume used for detecting topographic surfaces ($S_j$, for j=0, 1, 2, ..., 299) in the sample. More than or less than 300 slices can be used instead. A sector is cut out to emphasize that the volume has a thickness in the z-direction (down). The right side in the same box illustrates a motion volume at an instant of time where, as in FIGS. 1 and 3a, lighter gray represents axial positive and darker gray represents axial negative in arbitrary units. Next, 2D (two-dimensional) spatial frames are created by projection into the motion volume $V_z^{OCT}(\varepsilon,t)$. The structural volume comprises the illustrated stack of surfaces $S_0, S_1, \ldots, S_{299}$, and the motion volume comprises the illustrated time sequence of motion distributions for respective times $t_0, \ldots, t_1, \ldots, t_Q$. Then, temporal and spatial filtering is applied to each projection frame $\tilde{V}_z^{OCT}(\varepsilon,t)$. A temporal Fourier transform is applied to each spatial location $\varepsilon$ for the calculation of magnitude $A(\varepsilon)$ and phase $\Phi(\varepsilon)$. Subsequently the complex matrix $V_z(\varepsilon)=\sqrt{\pi/2}A(\varepsilon)e^{i\Phi(\varepsilon)}$ is formed for the local calculation of autocorrelation in a window of, e.g., 1×1 mm. The auto-correlation profile is fitted to Eq. 7 for the local estimation of wave number k*. Shear wave speed maps $c_s(\varepsilon)=\omega_0/k(\varepsilon)^*$ are calculated for each surface $S_j$ in the sample by moving the window through the entire projection frame, and by fixing the a priori known excitation frequency $\omega_0$. Finally, the compounding $c_s(\varepsilon)$ calculated at each surface $S_j$ as represented in the gray scale in the 3D map at upper right in FIG. 4, and the information may be appropriately stored or further processed.

Longitudinal shear wave propagation. Local speeds of LSW can be calculated using two methods: (1) time-of-flight approach for transient excitations and (2) correlation approach for harmonic excitations. The time-of-flight approach is based on space-time waveform tracking along the propagation direction. For a given x-axis position, the local group velocity of the wavefront $c_{LSW}$ is approximated by the slope of space-time curves within a window (W) along depth by $$c_{LSW}(z^w) = \frac{\Delta z}{\Delta t}, \quad \text{Eq. 8}$$

where $z^w$ is the location of the window in the z-axis, and $\Delta z$ is the distance traveled by the wavefront during time $\Delta t$ within the window along depth. Eq. 8 can be adapted to a least square regression approach as described in (13) for reducing noise and increasing accuracy in the estimation of wave speed. The sequential estimation of $c_{LSW}(z^w)$ along depth for each lateral position until the whole FOV is covered generates a 2D shear wave speed map (SWSM), also called an elastogram.

The correlation approach (for harmonic excitation), also referred to as Hoyt's method in (13, 14), leverages the complex-valued spatial particle velocity field $v_z^{Cplx}(x,z)$ obtained by: (1) Calculating the Fourier transform of the time signal at a given $(x_0,z_0)$ position: $\mathfrak{I}_{t_z}\{v_z(x_0,z_0;t)\}(x_0,z_0;\omega)$, and (2) evaluating the transformed signal at the angular frequency $\omega_0 = 2\pi f_0$, where $f_0$ is the excitation frequency: $v_z^{Cplx}(x_0,z_0) = \mathfrak{I}_{t_z}\{v_z(x_0,z_0;t)\}(x_0,z_0;\omega_0)$. Defining the z-axis as the LSW propagation direction, for a given lateral position $x_0$, the first lag of the auto-correlation function R of $v_z^{Cplx}$ using a kernel window of size L along depth is:

$$R(n,1) = \frac{1}{L-1} \sum_{m=0}^{L-2} \overline{v_z^{Cplx}(x_0, n+m)} v_z^{Cplx}(x_0, n+m+1), \quad \text{Eq. 9}$$

where $z_n = n\Delta_z$, for $n=0, 1, 3, \ldots, N-L-1$; where N is the number of samples along the z-axis, and $\Delta_z$ is the depth sampling resolution. Then, the local spatial wavenumber k can be estimated as:

$$k(x_0, z_n) = \frac{1}{\Delta_z} \arctan\left\{\frac{\text{Imag}\{R(n,1)\}}{\text{Real}\{R(n,1)\}}\right\}, \quad \text{Eq. 10}$$

where Real{•} and Imag{•} refer to the real and imaginary parts of a complex number. Subsequently, the LSW speed can be calculated as $c_{LSW}(x_0,z_n) = \omega_0/k(x_0,z_n)$. The sequential estimation of $c_{LSW}(x_0,z_n)$ along depth for each lateral position until the whole FOV is covered generates an elastogram (2D SWSM).

Experimental results of reverberant shear wave field. Numerical simulations discussed below show results of RevSW fields produced by MPE source and measured using a regular PhS-OCT system for the elastic characterization of tissues, also called Rev3D-OCE.

Validation of Rev3D-OCE fields in simulation using finite elements. Numerical simulations using a finite element model of cornea with four differentiated elastic layers (A, B, C, and D) demonstrate the capabilities of Rev3D-OCE method in layer detection compared to the conventional Lamb wave method. The layers were monotonically distributed from stiffer (A) to softer (D) using Young's moduli values based on the decreasing depth-dependent wave speed tendency reported in Wang et al, (1) for porcine cornea.

Figure 5A:
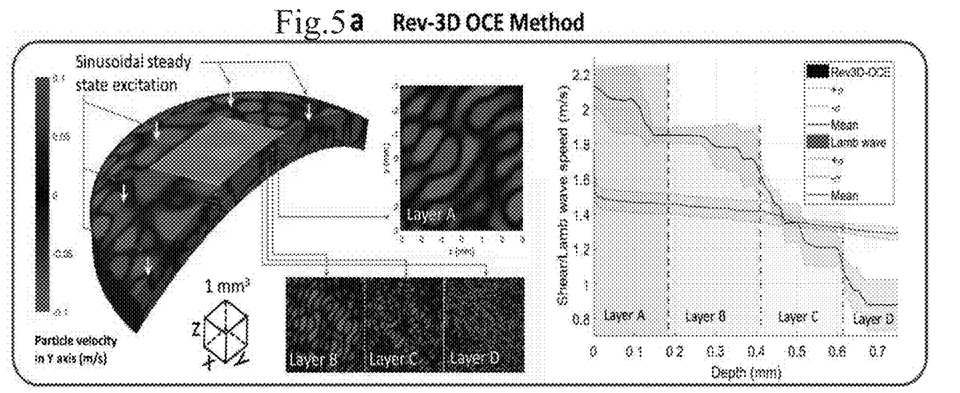
FIG. 5a shows the cornea model subjected to sinusoidal steady-state excitation of 2 kHz (Rev3D-OCE method) and FIG. 5b shows the cornea model subjected to axisymmetric Gaussian (σ=0.3 mm) transient (t=1 ms) force (Lamb wave method) producing a cylindrically-shaped Lamb wave propagation.
Figure 5B:
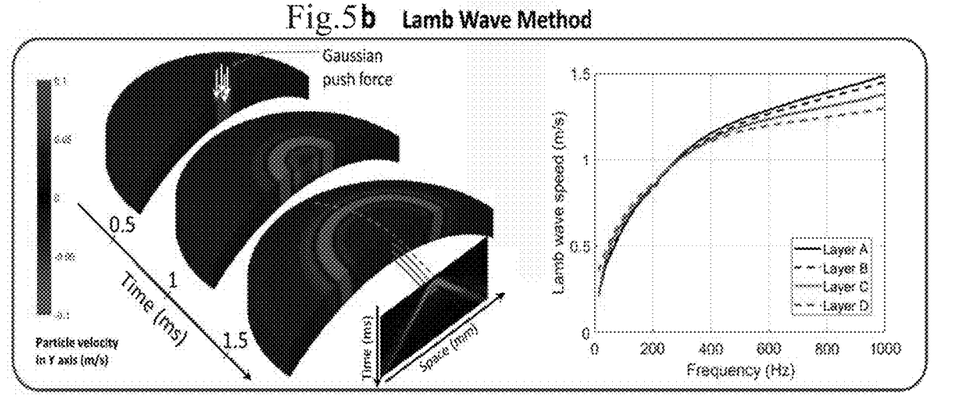

FIGS. 5a and 5b show numerical simulation results of a 3D finite element model of cornea composed of four layers with differentiated linear elastic materials. Again, particle velocity (motion) in illustrated in arbitrary units at an instant of time: red (axial positive), blue (axial negative) motion. FIG. 5a shows a cornea model subjected to sinusoidal steady-state excitation of 2 kHz (Rev3D-OCE method), and FIG. 5b shows the cornea model subjected to axisymmetric Gaussian ($\sigma=0.3$ mm) transient (t=1 ms) force (Lamb wave method) producing a cylindrically-shaped Lamb wave propagation. In FIG. 5a, the left portion shows a 3D volume of cornea subjected to sinusoidal steady-state excitation of 2 kHz through eight circular-distributed force heads, for example as illustrated in FIG. 2. As expected, wavelength changes in particle velocity along depth (z-axis) are detected and transformed into shear wave speed values using the reverberant theory, Eq. 7, and $c_s = \omega_0/k$, as shown in the right portion of FIG. 5a. In addition, shear wave speed values for each layer (A, B, C, D) are in good agreement with the layer material properties (2.5, 2, 1.3, 0.8 m/s), respectively, set in the simulation.

The Lamb wave method (typical transient excitation producing SAW in tissue) was also simulated by applying an axisymmetric Gaussian ($\sigma=0.3$ mm) transient (t=1 ms) force in the center of the layered cornea model producing a cylindrically-shaped Lamb wave propagation as shown in the left portion of FIG. 5b. Fourier analysis applied to space-time representations of wave propagation at each layer indicates that the antisymmetric zero order Lamb wave is the most predominant given the excitation shape and boundary conditions. FIG. 5b-right shows dispersion curves of Lamb wave speed calculated in each layer. As expected, for a selected frequency, the depth-dependent variation of Lamb wave speed is small compared to the Rev3D-OCE method shown in FIG. 5a-right. In addition, the Lamb wave speed depth profile has a decreasing tendency due to the high-low layer elasticity configuration. However, speed values are not in complete agreement with the layer material properties set in the simulation.

Figure 6A:
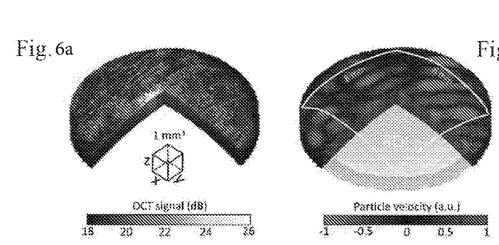
Figure 6B:
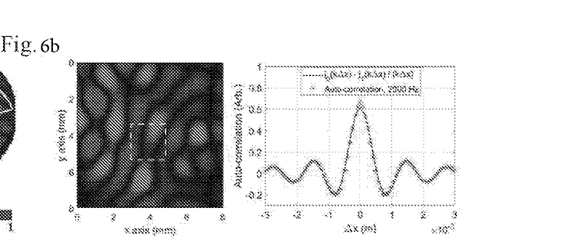
FIG. 6b-left shows a particle velocity frame extracted at the cornea epithelium compensated for the cornea curvature and FIG. 6b-right shows an auto-correlation plot taken along the x-axis in a section of this frame as fitted to Equation 7 and estimations of local wavenumber (k*), and, therefore, shear wave speed ($c_s$) using $c_s = \omega_0/k^*$, calculated for all depths from the top (epithelium) to bottom (endothelium) layers of cornea.

Elastic layer characterization of ex vivo porcine cornea using Rev3D-OCE. The Rev3D-OCE method enabled the elastic characterization of single layers in ex vivo porcine cornea with unprecedented contrast in the dynamic OCE field that matches the anatomical description of corneal layers. A fresh porcine eye cornea is subjected to a reverberant shear wave field of 2 kHz using a piezoelectric actuator attached to a 3D-printed ring with eight heads slightly touching the cornea surface and the motion (particle velocity) is detected using a PhS-OCT system. After the acquisition, a 3D reverberant cornea volume is obtained and shown in FIG. 6a. Reverberant frames of particle velocity are extracted following the surface of the cornea at all depths and the cornea curvature was compensated for. FIG. 6b shows a reverberant frame extracted at the top surface (epithelium) and indicates how the auto-correlation curve taken along the x-axis in a section of the frame fits the theoretical model, Eq. 7, of reverberant fields in elastic media. Then, estimations of local wavenumber (k*), and, therefore, shear wave speed ($c_s$) using $c_s = \omega_0/k^*$, are calculated for all depths from the top (epithelium) to the bottom (endothelium) layers of cornea.

Figure 6C:
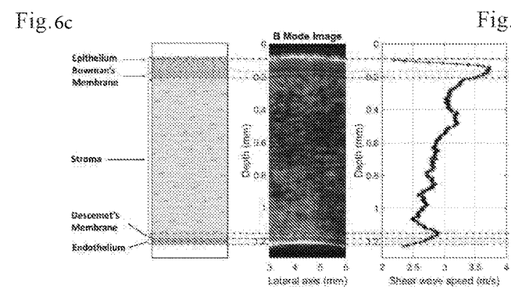
FIG. 6c shows depth-dependent shear wave speed profile of cornea and how it correlates with (1) structural information from the B-mode intensity image of the same cornea sample, and (2) the anatomical description of some of the corneal layers.
Figure 6D:
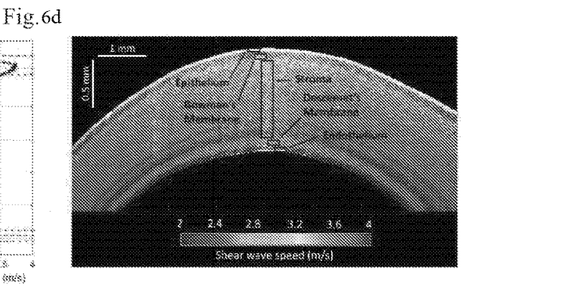
FIG. 6d shows a shear wave speed map profiled from the 3D volume in the xz-plane crossing the center of the cornea.

FIGS. 6a-6d show Rev3D-OCE results in ex vivo porcine cornea using a 2 kHz sinusoidal steady-state excitation and a PhS-OCT system. Once again, particle velocity (motion)

in illustrated in arbitrary units at an instant of time: red (axial positive), blue (axial negative) motion. FIG. 6a-left shows an acquired B-mode 3D volume, and FIG. 6a-right shows particle velocity reverberant volume of a cornea. FIG. 6b-left shows a particle velocity frame extracted at the cornea epithelium of the cornea of FIG. 6a) and compensated for the cornea curvature. The auto-correlation plot taken along the x-axis in a section of this frame is fitted to Eq. 7 and shown in FIG. 6b-right. Then, estimations of local wavenumber (k*), and, therefore, shear wave speed ($c_s$) using $c_s=\omega_0/k^*$, are calculated for all depths from the top (epithelium) to bottom (endothelium) layers of cornea. FIG. 6c shows the depth-dependent shear wave speed profile of cornea and how it correlates with (1) structural information from the B-mode intensity image of the same cornea sample, and (2) the anatomical description of some of the corneal layers. FIG. 6d shows a shear wave speed map profiled from the 3D volume in the xz-plane crossing the center of the cornea. Shear wave speed values for a selected cornea span from 2 m/s to 4 m/s (2 m/s min-to-max range) which is equivalent to 4 kPa and 16 kPa of shear modulus, respectively, if a density of $\rho=1000$ kg/m^3 is assumed in Eq. 1 and Eq. 2. FIG. 6d shows a shear wave speed map profiled from the 3D volume in the xz-plane crossing the center of the cornea. The level of contrast in layer detection of cornea achieved with the Rev3D-OCE method is unprecedented in the dynamic wave-based OCE field. Previous work using transient Lamb waves (15,16) shows depth-dependent wave speed profiles with reduced contrast (<0.3 m/s min-to-max range), and fewer numbers of features consistent with the anatomical description of corneal layers. Nevertheless, its decreasing tendency agrees with results reported by Rev3D-OCE and other approaches (17-20).

Figure 7:
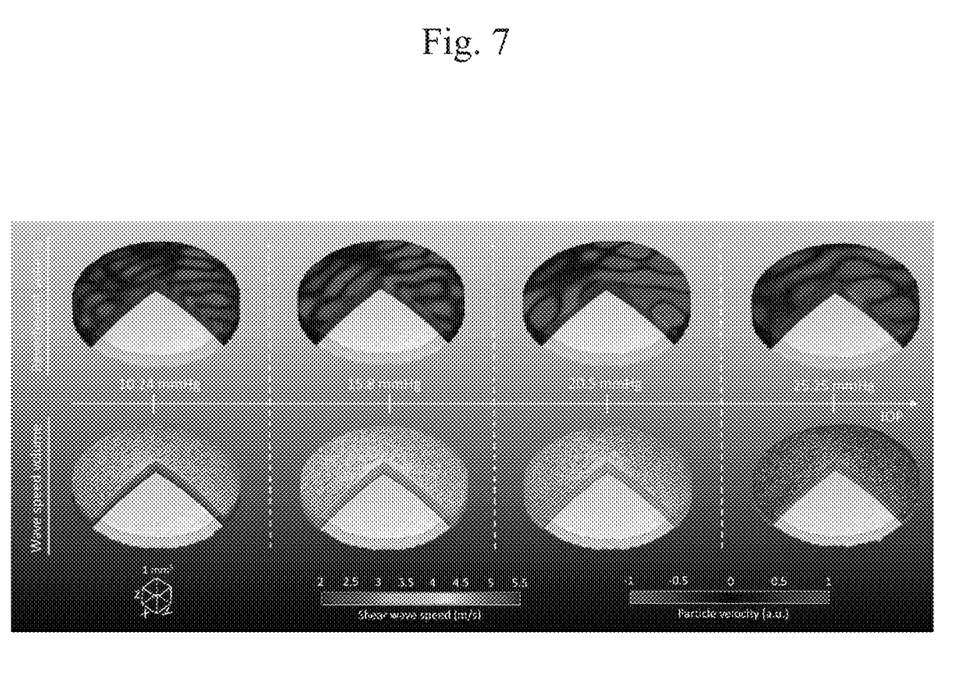
FIG. 7 shows Rev3D-OCE results in ex vivo IOP-controlled porcine cornea test. The top row shows particle velocity reverberant volumes of cornea subjected to four IOP levels: 10.24, 15.80, 20.50, and 25.25 mmHg. Particle velocity frames are extracted, following the curved shape of cornea at all depths, and processed using auto-correlation and fitted to Eq. 7 for the estimation of local wavenumber (k*). The bottom row shows shear wave speed volumes of cornea for each IOP case calculated using $c_s = \omega_0/k^*$.

Rev3D-OCE and Lamb wave methods vs. intraocular pressure (IOP) of cornea. Experiments in an IOP-controlled porcine eye cornea using the Rev3D-OCE and the conventional Lamb wave method for the detection of elastic layers demonstrate that Rev3D-OCE can monitor single corneal layer changes for different IOP levels. The top row in FIG. 7 shows reverberant volumes of cornea subjected to four IOP levels: 10.24, 15.80, 20.50, and 25.25 mmHg. The increasing tendency of wavelength in the reverberant patterns when the IOP level increases confirms the non-linear elastic nature of corneal tissue. Reverberant frames of particle velocity are extracted, following the curved shape of cornea at all depths, and processed using auto-correlation and the theoretical model, Eq. 7, of reverberant fields in elastic media. Then, local shear wave speed ($c_s$) is calculated for all depths from the top (epithelium) to the bottom (endothelium) layers of the cornea. The bottom row in FIG. 7 shows the shear wave speed volumes for each IOP level. It is evident that the shear wave speed increases with the IOP. The min-to-max range of speed change due to the application of different IOP levels is reported to be 3.5 m/s.

Figure 8:
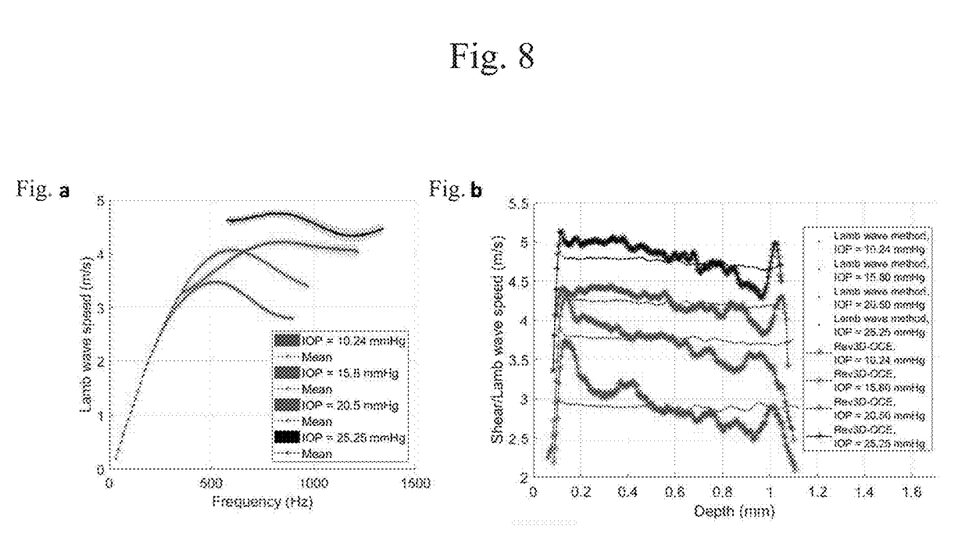

To explore the relationship between both methods, a Fourier analysis is applied to space-time representations of Lamb wave propagation at all layers for each IOP case, as shown in FIG. 8a. The shape of the dispersion curves indicates that the antisymmetric zero-order Lamb wave is the most predominant given the excitation shape and boundary conditions. This finding is in complete agreement with the simulations using a finite element analysis described above. Due to the nature of the Rev3D-OCE method, a single excitation frequency should be selected for further comparison with the Lamb wave method. Then, a frequency $f_0=800$ Hz, $\omega_0=1600\pi$ rad/s is chosen in order to cover for all four IOP cases in FIG. 8a, and depth-dependent Lamb wave speed profiles are plotted in FIG. 8b together with shear wave speed profiles obtained using the Rev3D-OCE method.

Figure 9:
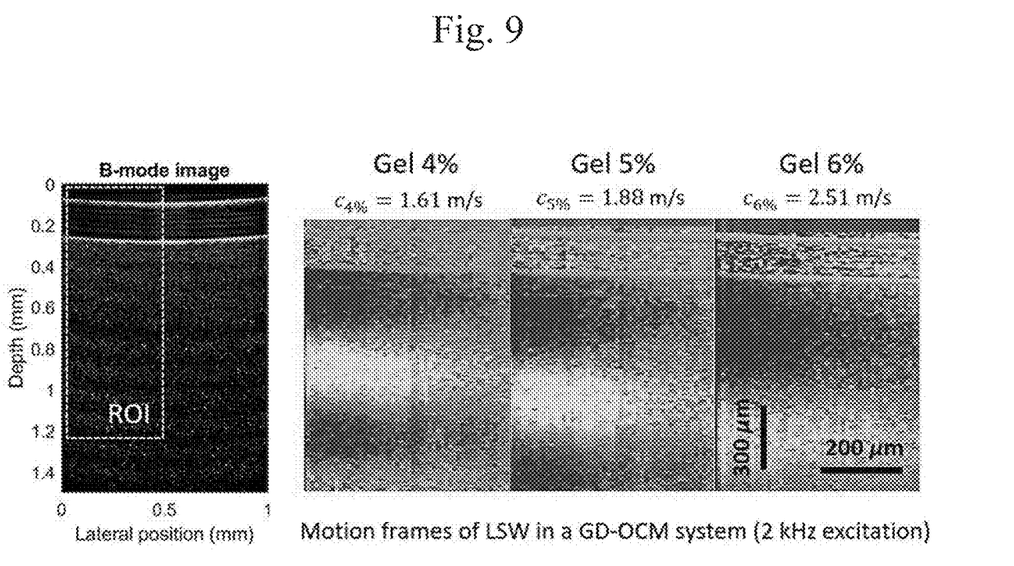
FIG. 9 shows structural at left and motion frames a right of LSW propagation in three phantom materials measured using GD-OCM.

Experimental results of longitudinal shear waves. The use of LSW fields produced by the CCE source and measured using the GD-OCM system for the elastic characterization of tissues is called LSW-OCE. Equipment such as in FIG. 3b can be used. Preliminary results in tissue mimicking phantoms demonstrate the capabilities of LSW-OCE. FIG. 9 shows motion frames of LSW propagation in three phantom materials: 4%, 5% and 6% gelatin concentrations (ground truth shear wave speed values are shown for each case). The region of interest (ROI) covers an area of 1×1.5 mm² with a resolution of 3 μm approximately.

Figure 10:
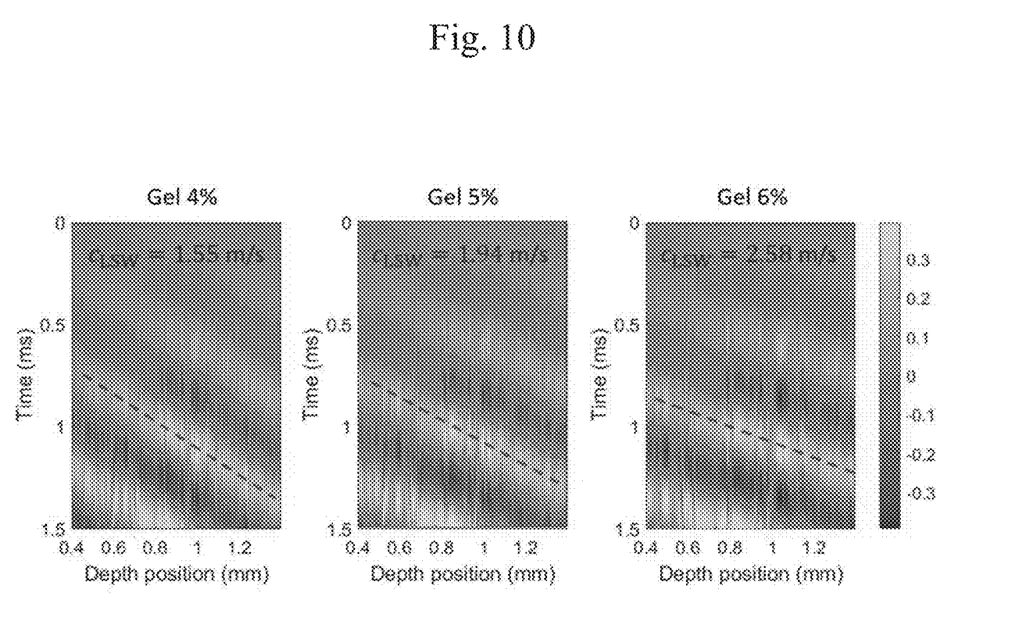
FIG. 10 shows spatio-temporal analysis of LSW propagation in three phantom materials. The LSW speed is calculated in each case. The color bar represents displacement in arbitrary units.

In FIG. 10, spatio-temporal analysis of LSW propagation is conducted over a 0.5×1.2 mm region of interest (ROI region in FIG. 9). Results show differentiated LSW speed for each phantom material: 1.55±0.07 m/s (3%), 1.94±0.06 m/s (4%), and 2.58±0.08 m/s (5%). These results point to LSW-OCE as a promising technique to characterize microstructures for clinical applications.

The systems and methods disclosed in this patent specification can be useful in various application areas, in medical and industrial fields, as well as research in life sciences including in vivo studies. These broad categories include but are not limited to: Eye, Skin, Brain, and Polymers.

In the eye category, applications include studies and help in diagnosing and treating conditions such as: (a) Keratoconus and Ectasia, see https://eyewiki.aao.org/Corneal_Biomechanics#Keratoconus "Disruption of the corneal fiber network by disease or surgery can result in decreased structural integrity of the cornea, degeneration, surface irregularities, and distorted vision. Understanding the specific processes of corneal degeneration allows for targeted treatments to be developed and administered to effected patients." "Keratoconus is a progressive ectatic disorder of the cornea characterized by bilateral, asymmetric, non-inflammatory degeneration which results in central and paracentral thinning and protrusion. Progression of the disease is thought to begin with focal degeneration of material properties, followed by a cycle of thinning, increased strain, and redistribution of stress. While collagen composition, distribution, and packing appear normal in keratoconus, the native collagen network is mostly unorganized. Irregularities in the collagen network result in distortion of refractive function which can lead to high myopia and irregular astigmatism. Keratoconus corneas also exhibit increased levels of collagenolysis, loss of keratocytes, reduced collagen cross-links, and significantly weakened stress-versus-strain responses. Factors potentially contributing to the biomechanical degeneration of diseased corneas include genetics, contact lens microtrauma, eye rubbing, and atopy; (b) Iatrogenic corneal ectasia, which is a rare complication of refractive surgery thought to be the result of inadequate residual stromal bed left after surgery or surgery performed on a cornea with unidentified keratoconus. Iatrogenic ectasia is characterized by biomechanical degeneration with progressive steepening of the cornea and a very thin stromal bed (<300 μm). The result is progressive corneal steepening which leads to myopic shift, irregular astigmatism, and reduced visual acuity. Evaluation of ectatic corneas reveals a normal thickness laser-assisted in situ keratomileusis (LASIK) flap, Bowman's layer breaks, thin residual stromal beds, reduced number and thickness of lamellae, and larger than normal residual artifacteous intralamellar clefts in the elastic region. The main risk factor for iatrogenic ectasia is irregular topography preoperatively, including asymmetric inferior corneal steepening or asymmetric bowtie patterns with skewed steep radial axes above and below the horizontal meridian.[38][39] In addition, thin residual stromal beds (225-250 μm), high myopia, young age at operation, and deep ablations have been identified as risk factors. Combined screening programs that include tomographic and topographic evaluation are suggested preoperatively to prevent iatrogenic ectasia, but detection of at-risk corneas remains a challenge. "See https://www.ncbi.nlm.nih.gov/pubmed/30359155 and https://www.ncbi.nlm.nih.gov/pmc/articles/PMC4844427/ (c) Corneal Crosslinking, see https://eyewiki.aao.org/Corneal_Collagen_Cross-Linking: "Corneal collagen crosslinking is a technique which uses UV light and a photosensitizer to strengthen chemical bonds in the cornea. The goal of the treatment is to halt progressive and irregular changes in corneal shape known as ectasia. These ectatic changes are typically marked by corneal thinning and an increase in the anterior and/or posterior curvatures of the cornea, and often lead to high levels of myopia and astigmatism. The most common form of ectasia is keratoconus and less often ectasia is seen after laser vision correction such as LASIK." (d) Refractive Surgery: LASIK, see https://eyewiki.aao.org/LASIK_for_Myopia_and_Astigmatis%3A_Saftey_and_Efficacy#Introduction "LASIK (laser in situ keratomileusis) is the most frequently performed of many surgical procedures designed to correct refractive errors. LASIK involves creating a corneal flap using a microkeratome or a femtosecond laser, reshaping the cornea using an Excimer laser to remove tissue from the underlying stromal bed and then replacing the flap. Corneal ectasia is one of the most devastating complications after LASIK. Post-LASIK ectasia is considered in patients who developed increasing myopia, with or without increasing astigmatism, loss of uncorrected visual acuity, often loss of best-corrected visual acuity, with keratometric steepening, with or without central and paracentral corneal thinning, and topographic evidence of asymmetric inferior corneal steepening after LASIK procedure. Understanding and imaging the biomechanical properties of the patient's cornea prior to LASIK can be a valid approach to predicting if the patient's eye will develop post-LASIK ectasia." (e) Refractive Surgery: LIRIC, see https://www.bioopticsworld.com/biomedicine/article/16429510/ophtalmologyfemtosecond-lasers-liric-nextgeneration-refractive-laser-surgery. LIRIC (laser induced refractive index change) is a promising much less invasive approach that overcomes limitations of LASIK. Monitoring the biomechanical properties as the cornea prior, during and after LIRIC would offer control and guidance on how to tailor the treatment to each patient. (f) Glaucoma, see https://www.glaucoma.org/glaucoma/symptoms-of-primary-open-angle-glaucoma.php. In open-angle glaucoma, the angle in your eye where the iris meets the cornea is as wide and open as it should be, but the eye's drainage canals become clogged over time, causing an increase in internal eye pressure (IOP) and subsequent damage to the optic nerve. Studies conducted in Singh, el at. (2017)[1] and Ambrozinski, et al. (2016)[2], demonstrated a direct relationship between elasticity (Young's modulus) of cornea measured using OCE and IOP levels. Therefore, OCE can be used as a tool for the indirect monitoring of abnormal IOP levels in the eye, and, therefore, the early diagnosis of glaucoma. See [1] M. Singh, Z. Han, A. Nair, A. Schill, M. D. Twa, and K. V. Larin, "Applanation optical coherence elastography: noncontact measurement of intraocular pressure, corneal biomechanical properties, and corneal geometry with a single instrument," BIOMEDO 22, 20502-20502 (2017); [2] L. Ambroziński, S. Song, S. J. Yoon, I. Pelivanov, D. Li, L. Gao, T. T. Shen, R. K. Wang, and M. O'Donnell, "Acoustic micro-tapping for non-contact 4D imaging of tissue elasticity," Scientific Reports 6, 38967 (2016). (f) Lamina cribrosa—diaphragm regulating pressure between the eye and the brain, see https://www.ncbi.nlm.nih.gov/pubmed/29049736. (g) Presbyopia, see https://nei.nih.gov/health/errors/presbyopia. Presbyopia is a condition associated with the aging of the eye that results in progressively worsening ability to focus clearly on close objects. It is due to hardening of the crystalline lens of the eye causing the eye to focus light behind rather than on the retina when looking at close objects. Current investigation using femtosecond—lasers induce cuts in the lens lead to a gain in lens elasticity. This might be a possibility for presbyopia treatment in phakic eyes. (1) Therefore, measuring mechanical properties of crestline lens is fundamental of monitoring such disease and the treatment. (h) OCE has also been used to study the mechanical properties of the crystalline lens. (2) However, the crystalline lens is located inside the eye, making in vivo measurements difficult; and possesses a much more complicated geometry which creates unique challenges for elastography. See [1] U. Oberheide, T. Ripken, S. Schumacher, M. Fromm, G. Gerten, H. Lubatschowski; Increase Of The Elasticity In Crystalline Lenses After Treatment With Femtosecond Laser Pulses. *Invest. Ophthalmol. Vis. Sci.* 2006; 47(13):5889; [2] C. Wu, Z. Han, S. Wang, J. Li, M. Singh, C.-H. Liu, S. Aglyamov, S. Emelianov, F. Manns, and K. V. Larin, "Assessing age-related changes in the biomechanical properties of rabbit lens using a coaligned ultrasound and optical coherence elastography system," Investigative ophthalmology & visual science 56, 1292-1300 (2015).

Several companies are known to work in the eye category. They include (a) Reichert Inc. The Ocular Response Analyzer (ORA) (Reichert Inc., Depew, N.Y.), described by Luce et al, is the only commercially available medical device capable of measuring corneal biomechanics in vivo. See https://www.reichert.com; (b) Intelon https://www.intelon.com/. Intelon Optics is a medical device company developing the Brillouin Optical Scanner System (BOSS™), a technology that enables next-generation point-by-point biomechanics imaging of eye structures, extending from the cornea to the posterior part of the globe; and Oculus, see https://www.oculus.de/. The Corvis® STL is said to record the reaction of the cornea to a defined air pulse with a newly developed high-speed Scheimpflug-camera that takes over 4,300 images per second. IOP and corneal thickness can be measured based on the Scheimpflug images.

In the skin category, measuring the biomechanical properties of skin has applications in dermatology (i.e., scleroderma, cancer) and in cosmetics (to assess effectiveness of products). "Progression of skin sclerosis disturbs normal skin architecture and compromises biomechanical skin properties. Biomechanical assessment of normal skin has shown that the skin has the unique ability to deform under low pressures (extensibility). When the load is increased further, skin shows resistance to stress (stiffness—Young's modulus) but continues to stretch even under stable pressure (viscoelasticity). Skin has a strong tendency to resume its original shape and dimensions after release of the stretching force (elasticity). In vivo studies have shown changes in extensibility, stiffness, and elasticity in different sexes and ages, which in part may be attributed to differences in skin thickness. Clinical conditions affecting the fibre framework of skin are likely to alter its biomechanical properties." See https://ard.bmj.com/content/61/3/237. OncoRes Medical, see https://www.oncoresmedical.com/, is believed to be developing an intraoperative imaging technology that translates the surgeon's sense of touch into a microscale image to improve surgical accuracy and reduce complication rates.

In the brain category, the systems and methods described in this patent specification can be useful in studies and treatment of Alzheimer, small vessel disease, and traumatic injury.

In the polymers category, the systems and methods described in this patent specification can be useful in developing and improving contact and intraocular lenses and materials such as W. L. Gore's GORE® TAG® Conformable Thoracic Stent Graft for Thoracic Endovascular Aortic Repair self-healing polymers.

Although the foregoing has been described in some detail for purposes of clarity, it will be apparent that certain changes and modifications may be made without departing from the principles thereof. There can be many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

REFERENCES

1. Schmitt, J. M., "OCT elastography: imaging microscopic deformation and strain of tissue," Opt. Express 3(6), 199-211 (1998).
2. Wang, S., and Larin, K. V., "Optical coherence elastography for tissue characterization: a review," Journal of biophotonics 8(4), 279-302 (2015).
3. Mulligan, J. A., Untracht, G. R., Chandrasekaran, S. N., Brown, C. N., and Adie, S. G., "Emerging Approaches for High-Resolution Imaging of Tissue Biomechanics With Optical Coherence Elastography," IEEE Journal of Selected Topics in Quantum Electronics 22(3), 246-265 (2016)
4. Larin, K. V., and Sampson, D. D., "Optical coherence elastography OCT at work in tissue biomechanics [Invited]," Biomed. Opt. Express 8(2), 1172-1202 (2017).
5. Kirby, M. A., Pelivanov, I., Song, S., Ambrozinski, L., Yoon, S. J., Gao, L., Li, D., Shen, T. T., Wang, R. K., and O'Donnell, M., "Optical coherence elastography in ophthalmology," J Biomed Opt 22(12), 1-28 (2017).
6. Parker, K. J., Doyley, M. M., and Rubens, D. J., "Imaging the elastic properties of tissue: the 20 year perspective," Physics in Medicine & Biology 56(1), R1 (2011).
7. Streitberger, K.-J., Reiss-Zimmermann, M., Freimann, F. B., Bayerl, S., Guo, J., Arlt, F., Wuerfel, J., Braun, J., Hoffmann, K.-T., and Sack, I., "High-Resolution Mechanical Imaging of Glioblastoma by Multifrequency Magnetic Resonance Elastography," PLOS ONE 9(10), e110588 (2014).
8. Egle, D. M., "Diffuse wave fields in solid media," The Journal of the Acoustical Society of America 70(2), 476-480 (1981).
9. U.S. Pat. No. 8,340,455
10. Zvietcovich, F., Rolland, J. P., and Parker, K. J., "An approach to viscoelastic characterization of dispersive media by inversion of a general wave propagation model," Journal of Innovative Optical Health Sciences 10(06), 1742008 (2017).
11. Song, S., Huang, Z., and Wang, R. K., "Tracking mechanical wave propagation within tissue using phase-sensitive optical coherence tomography: motion artifact and its compensation," BIOMEDO 18(12), 121505 (2013).
12. Parker, K. J., Ormachea, J., Zvietcovich, F., and Castaneda, B., "Reverberant shear wave fields and estimation of tissue properties," Phys Med Biol 62(3), 1046-1061 (2017).
13. Zvietcovich, F., Rolland, J. P., Yao, J., Meemon, P., and Parker, K. J., "Comparative study of shear wave-based elastography techniques in optical coherence tomography," BIOMEDO 22(3), 035010-035010 (2017).
14. Hoyt, K., Castaneda, B., and Parker, K. J., "Two-Dimensional Sonoelastographic Shear Velocity Imaging," Ultrasound in Medicine & Biology 34(2),
15. Wang, S., and Larin, K. V., "Noncontact depth-resolved micro-scale optical coherence elastography of the cornea," Biomed. Opt. Express 5(11), 3807-3821 (2014).
16. Singh, M., Li, J., Han, Z., Vantipalli, S., Liu, C. H., Wu, C., Raghunathan, R., Aglyamov, S. R., Twa, M. D., and Larin, K. V., "Evaluating the Effects of Riboflavin/UV-A and Rose-Bengal/Green Light Cross-Linking of the Rabbit Cornea by Noncontact Optical Coherence Elastography," Invest Ophthalmol Vis Sci 57(9), OCT112-120 (2016).
17. Scarcelli, G., Pineda, R., and Yun, S. H., "Brillouin Optical Microscopy for Corneal Biomechanics," Investigative Ophthalmology & Visual Science 53(1), 185-190 (2012).
18. Nahas, A., Bauer, M., Roux, S., and Boccara, A. C., "3D static elastography at the micrometer scale using Full Field OCT," Biomed Opt Express 4(10), 2138-2149 (2013).
19. Hollman, K. W., Emelianov, S. Y., Neiss, J. H., Jotyan, G., Spooner, G. J. R., Juhasz, T., Kurtz, R. M., and O'Donnell, M., "Strain Imaging of Corneal Tissue With an Ultrasound Elasticity Microscope," Cornea 21(1), 68-73 (2002).
20. Shih, C.-C., Huang, C.-C., Zhou, Q., and Shung, K. K., "High-Resolution Acoustic-Radiation-Force-Impulse Imaging for Assessing Corneal Sclerosis," IEEE transactions on medical imaging 32(7), 1316-1324 (2013).

The invention claimed is:

1. A Gabor domain optical coherence elastography system comprising:
   a source configured to induce longitudinal shear waves (LSW) in a three-dimensional (3D) field of view (FOV) in an object;
   a Gabor domain optical coherence microscope configured to observe the object and to detect displacement of locations said FOV in the object over a selected time interval in the presence of said LWS in the object; and
   a processor system configured to computer-process said displacements to derive and display elastographic properties of said FOV of the object.

2. The system of claim 1 in which said source inducing LWS in the object comprises a coverslip contacting the object over said FOV.

3. The system of claim 1, in which said object is cornea of an eye.

4. The system of claim 1, in which the object is a patient's skin.

5. The system of claim 1, in which the object is brain tissue.

* * * * *